United States Patent [19]

Hayashi et al.

[11] Patent Number: 5,585,365
[45] Date of Patent: Dec. 17, 1996

[54] ANTIVIRAL POLYSACCHARIDE

[75] Inventors: Toshimitsu Hayashi; Kyoko Hayashi, both of Imizu-gun; Ichiro Kojima, Yokosuka, all of Japan

[73] Assignee: Nippon Oil Co., Ltd., Tokyo, Japan

[21] Appl. No.: 273,095

[22] Filed: Jul. 8, 1994

[30] Foreign Application Priority Data

Jul. 27, 1993 [JP] Japan .................. 5-185055

[51] Int. Cl.⁶ .................. A01N 43/04; A01N 61/00; A23G 3/00; A61K 39/12
[52] U.S. Cl. .................. 514/54; 514/1; 514/23; 514/934; 514/885; 514/888; 514/896; 426/658; 424/204.1; 424/206.1; 424/208.1; 424/184.1; 424/212.1; 424/230.1; 424/479
[58] Field of Search .................. 514/58, 885, 888, 514/896, 54, 1, 23, 934; 424/442, 439, 204.1, 206.1, 208.1, 184.1, 212.1, 230.1, 479; 426/658

[56] References Cited

U.S. PATENT DOCUMENTS

| | | |
|---|---|---|
| 3,983,008 | 9/1976 | Shinozaki et al. .................. 195/104 |
| 4,021,303 | 5/1977 | Nakabayashi .................. 426/656 |
| 4,522,814 | 6/1985 | Nonomura et al. .................. 514/54 |
| 4,744,996 | 5/1988 | Rakow et al. .................. 426/804 |
| 4,840,941 | 6/1989 | Ueno et al. .................. 514/54 |
| 4,857,325 | 8/1989 | Albeck et al. .................. 424/195.1 |
| 4,897,266 | 1/1990 | Herve et al. .................. 424/195.1 |
| 4,986,985 | 1/1991 | Grossman et al. .................. 514/934 |
| 5,100,879 | 3/1992 | Ueno et al. .................. 514/54 |
| 5,229,146 | 7/1993 | Tanaka .................. 426/805 |

*Primary Examiner*—John Kight
*Assistant Examiner*—Louise Leary
*Attorney, Agent, or Firm*—Seed and Berry LLP

[57] ABSTRACT

An antiviral polysaccharide purified from an extract prepared by extracting Spirulina cells with hot water, having the following properties:

(1) it comprises rhamnose, glucose, fructose, ribose, galactose, xylose, mannose, glucuronic acid and galacturonic acid;

(2) it exhibits an absorption at 480 nm in phenolsulfuric acid reaction; and (3) it has a molecular weight of 250,000 to 300,000 Daltons as determined by gel filtration; and pharmaceuticals, food and feed, comprising said antiviral polysaccharide.

10 Claims, No Drawings

ANTIVIRAL POLYSACCHARIDE

BACKGROUND OF THE INVENTION

1. Field of the Invention

The present invention relates to an antiviral polysaccharide purified from an extract prepared by extracting Spirulina cells with hot water (designated Spirulina polysaccharide hereinafter), as well as pharmaceutical compositions, foods and drinks, feeds and food additives, especially functional foods and drinks, comprising said antiviral composition.

2. Related Art

Although antiviral compositions derived from materials which have been used for long time and whose safety has been confirmed, especially antiviral composition useful as active ingredients for pharmaceuticals or functional foods are sought, satisfactory composition have not yet been known.

Although Spirulina has been used as foods or drinks, or a component thereof, its antiviral activity is not known.

Spirulina is reported to have activities to lower blood sugar level in the diabetes, to lower blood cholesterol, to alleviate the symptoms of gastric ulcer and gastritis, exhibit antiallergic action, to be effective for treatment of cataract, etc. However, the inventors are not aware of report which suggests that Spirulina contains antiviral substance.

SUMMARY OF THE INVENTION

Accordingly, the present invention provides an antiviral polysaccharide purified from an extract prepared by extracting Spirulina cells with hot water, as well as pharmaceutical compositions, foods and drinks, feeds, and food additives, especially functional foods, comprising said antiviral composition.

The present invention further provides a method for prophylactic or therapeutic treatment of viral diseases.

More specifically the present invention provides an antiviral polysaccharide having the following properties:

(1) it comprises rhamnose, glucose, fructose, ribose, galactose, xylose, mannose, glucuronic acid and galacturonic acid;

(2) it exhibits an absorption at 480 nm in phenolsulfuric acid reaction; and (3) it has a molecular weight of 250,000 to 300,000D as determined by gel filtration method.

The present invention also provides an antiviral pharmaceutical composition comprising as its active ingredient said antiviral composition, and pharmaceutically acceptable conventional carrier.

The present invention further provides a food additive comprising said antiviral composition.

The present invention further provides foods or drinks, especially functional foods, comprising said antiviral composition.

The present invention still more provides a feed comprising said antiviral composition.

More preferably, the present invention provides a method for prophylactic or therapeutic treatment of viral diseases comprising administering said antiviral composition to a subject to be treated.

DETAILED DESCRIPTION OF THE INVENTION

In the present invention, "Spirulina" means algae belonging to the genus Spirulina, and includes any species containing the present antiviral substance soluble in hot water. Preferably, the Spirulina is those belonging to the species *Spirulina platensis,* which has been used as foods etc.

The Spirulina cells used as a starting material for preparing the present antiviral composition may be living or wet cells, or dry cells. To extract the present antiviral polysaccharide from the Spirulina cells, the Spirulina cells are suspended in water, preferably, distilled water, deionized water or other purified water, and heated at a temperature between 70° C. and 100° C., and preferably between 80° C. and 95° C., and maintained for 10 to 120 minutes, preferably 40 to 60 minutes. Preferably the suspension is stirred continuously or periodically during the extraction. Alternatively, the Spirulina cells are suspended in water already heated as described above, and the suspension is incubated as described above. Preferably the extraction container has a vapor condenser to condense a vapor and to return the condensed water to the suspension so that the amount of water in the suspension is maintained at a constant level during the extraction. Alternatively, fresh hot water is added to the suspension to maintain a volume of the suspension during the extraction.

After the first extraction, the suspension is centrifuged or filtered according to a conventional procedure to obtain a supernatant or filtrate and cells. The recovered cells are suspended in water, and the above-mentioned extraction procedure is preferably repeated as the second extraction. Similarly, the third extraction is preferably carried out. The supernatants or filtrates obtained by the above-mentioned extractions are combined to obtain an extract.

In the above extraction procedures, concentration of Spirulina cells in the suspension is not critical and for example 5 to 50% by weight, and preferably 30 to 40% by weight. Where the concentration is too high recovery of the extract is low, while where the concentration is too low a concentration of an active ingredient in the extract is low, resulting in high cost for recovery of the active ingredient from the extract such as for evaporating off of water from the extract.

After the extractions, the extract is preferably concentrated to obtain a concentrate, or further concentrated and dried to obtain a dry extract. These concentration and drying are carried out according to conventional procedures such as concentration under a reduced pressure, spray drying, lyophilization etc.

The Spirulina extract thus obtained is used to prepare an aqueous solution of the extract, to which then was added a protein precipitating agent such as trichloroacetic acid to a concentration of, for example 10% trichloroacetic acid, allowing precipitation of proteins in the extract. The precipitate is removed by a conventional procedure such as centrifugation or filtration to recover a supernatant or filtrate. Next, the protein precipitating agent such as trichloroacetic acid is eliminated by a conventional procedure such as dialysis, diafiltration etc. to obtain a protein-free extract, which is lyophilized if desired.

The extract thus obtained is used to prepare an aqueous solution, which is then applied to a purification process such as column chromatography using Toyopearl, DEAE cellulose, Sepharose etc. to obtain fractions. Fractions which show a single peak at 480 nm in phenol sulfuric acid reaction are selected, and if desired subjected to conventional concentration, purification and/or drying procedures such as concentration under a reduced pressure, dialysis, diafiltration, lyophilization etc. to obtain white powder.

The substance thus obtained has the following properties:

(1) this substance exhibited yellow color showing a maximum absorption at 480 nm when concentrated sulfuric acid containing 10% phenol was added to an aqueous solution of the present substance, and immediately stirred.

(2) this substance was dissolved in trifluoroacetic acid, and the solution was sealed in a tube under a reduced pressure and treated in a thermostat container at 100° C. for 6 hours to hydrolyze the substance, and the was analyzed for sugars. As a result, rhamnose, glucose, fructose, ribose, galactose, xylose, mannose, glucuronic acid and galacturonic acid were detected.

(3) the substance showed a molecular weight of 250,000 to 300,000 Daltons as determined by gel filtration.

(4) the elements S, P, Ca and Mg were detected in addition to the elements C, H and N. Therefore, the present substance may be polysaccharide to which sulfate and phosphate are bonded (Spirulina polysaccharide).

The present invention relates to an antiviral pharmaceutical composition comprising said Spirulina polysaccharide. The antiviral pharmaceutical is preferably orally administered to a subject such as human or animal. Administration dose for human is about 5 to 200 mg/kg body weight·day. Administration dose for animals other than human is similar to that for human. The present pharmaceutical composition may be liquid, powders, capsules and the like. These formulations can be prepared according to conventional formulation procedures using conventional oral excipients such as starch, lactose, carboxymethylcellulose and the like.

The present invention further relates to foods or drinks, or food or drink additives, especially functional foods, comprising the antiviral Spirulina polysaccharide. These foods and drinks include, for example, chocolate drinks, tea, nutrient-enriched drinks, spices, biscuits, hamburgers, and the like. An amount of Spirulina polysaccharide added to a food or drink varies dependent on the kind of foods or drinks and usually 1 g/kg to 100 g/kg.

The present invention also relates to feeds comprising the Spirulina polysaccharide. The feeds contain, for example, 1 g/kg to 100 g/kg of the polysaccharide.

The present invention still more relates to a method for prophylactic or therapeutic treatment of viral diseases, comprising administrating the present antiviral Spirulina polysaccharide to a subject which needs antiviral prophylactic or therapeutic treatment.

The subjects to be treated include humans, animals other than human; such as domestic animals such as cattles, pigs, sheeps, goats, and the like; pets such as dogs, cats, and the like.

Viruses to be treated by the present antiviral Spirulina polysaccharide include various viruses which cause diseases in human and other animals, for example, herpes viruses such as herpes simplex virus, human cytomegalovirus, measles virus, pox virus, influenza virus, mumps virus, HIV, hepatitis A virus, and the like.

The antiviral Spirulina polysaccharide is administered, preferably orally at a dose of about 5 mg/kg weight·day to about 200 mg/kg weight·day, depending on general conditions, severity of the diseases, and the like. The antiviral Spirulina polysaccharide may be administered in the above-mentioned various formulations, such as pharmaceutical compositions, foods or drinks; feeds, and the like.

EXAMPLES

Next, the present invention is explained in more detail by Examples. However, the scope of the invention is not limited to the following Examples.

EXAMPLE 1

Production of Spirulina polysaccharide

Dry cell powder 200 g of *Spirulina platensis* was heated in 250 ml of hot water (95° to 100° C.) for one hour for extraction, the heat-treated suspension was filtered to remove the cells and to recover a filtrate, i.e., an aqueous extract, which was then evaporated off under a reduced pressure, and further lyophilized to obtain 9.2 g of powder.

One g of the powder was dissolved in 100 ml of a 10% aqueous solution of trichloroacetic acid, and the solution was allowed to put in a refrigerator overnight to allow formation of precipitate, which was then eliminated by centrifugation to recover a supernatant. The supernatant in a cellophane tube was dialyzed against water overnight to obtain a dialysate, which was then lyophilized to obtain a lyophilizate. The lyophilizate was dissolved in distilled water and the solution was subjected to column chromatography using Toyopeal HW-60S (elute: water), DEAE cellulose (elute: 0.5M sodium chloride aqueous solution), and Sepharose 6B (elute: 0.01M citrate buffer, pH 7.0, containing 0.1M sodium chloride). Detection was carried out by phenol-sulfuric acid method, and finally, 20 mg of a fraction exhibiting high antiviral activity was obtained as an antiviral Spirulina polysaccharide.

EXAMPLE 2

Antiviral activity test

The polysaccharide preparation obtained in Example 1 was tested for its antiviral activity. The test was carried out by a procedure described in K. Hayashi et al., Antiviral Research 9: 345–354 (1988).

A cytotoxic test was carried out as follows. HeLa cells were cultured in a 24-well plate to subconfluent state at 37° C. for 24 hours, the spent medium was replaced with 200 μl/well of a fresh medium (MEM supplemented with 5% fetal bovin serum) containing a varying concentration of the polysaccharide. After culturing at 37° C. for 72 hours, cells were peeled off with 0.05% trypsin, and stained with Trypan blue to count living cells. A ratio of living cells cultured in a medium to which test sample was added was calculated by taking as 100% the number of living cells cultured in a control medium to which a test sample was not added.

Next, a concentration of a test sample which provides 50% growth inhibition ($ID_{50}$) was obtained using a semilogarithmic graph.

An antiviral activity was determined by a virus yield reduction method described below: Host cells were cultured in a 24-well plate to form a single layer of the cells, which were then washed, and infected with 0.5 m.o.i. of virus at a room temperature for one hour. 300 μl of a medium (MEM+ 2% fetal bovin serum) containing a test sample in a different concentration was added to each well, and the culturing was continued in 5% $CO_2$, at 34° C. for 24 hours. The cells were disrupted by three repeats of freezing and thawing of the cells, and the number of viruses was counted by plaque assay. The plaques assay was two times repeated. The concentration of a test sample which reduces the number of plaque by 50% compared to a control test not using the test sample is expressed as $ED_{50}$.

The result is shown in Table 1.

TABLE 1

Antiviral activity and cytotoxity of Spirulina polysaccharide

| Viruses | Host cells | Cytotoxity ($ID_{50}$: μg/ml) | Antiviral Activity ($ED_{50}$: μg/ml) | Therapeutic factor ($ID_{50}/ED_{50}$) |
|---|---|---|---|---|
| Herpes symplex I | HeLa | >5000 | 3.9 | >1280 |
| Human cytomegalovirus | HEL | >5000 | 3.1 | >1610 |
| Measles virus | Vero | >5000 | 3.8 | >1310 |
| Mumps virus | Vero | >5000 | 11 | >450 |
| Influenza virus | MDCK | >5000 | 87 | >57 |

HeLa: Cells derived from human utero cervical cancer
HEL: Human embrio lung cells
Vero: Cells derived from the kidney of African green monkey
MDCK: Cells derived from dog kidney

EXAMPLE 3

Effect of antiviral polysaccharide on human immunodeficiency virus (HIV)

Antiviral activity of the polysaccharide obtained in Example 1 on human immunodeficiency virus (HIV) was tested. $1\times10^6$ non-infected Molt-4 cells, and the same number of cells persistently infected with HIV, i.e., Molt-4/$HTLV_{IIIB}$ were cocultured with an aqueous solution of the polysaccharide at 37° C. for 24 hours, and syncytium formation was expressed by Fusion Index. The result is shown in Table 2. The present polysaccharide inhibited the sincytium formation at a concentration of 30 μg/ml.

TABLE 2

Inhibitory action of Spirulina polysaccharide on sincytium formation from cells consistently infected with HIV (Fusion Index)

| | Concentration of polysaccharide (μg/ml) | | | | |
|---|---|---|---|---|---|
| | 0 | 1.5 | 7 | 30 | 150 |
| Fusion Index | 2.8 | 3.3 | 2.0 | 0.3 | 0.2 |

EXAMPLE 4

Formulation of pharmaceutical

A pharmaceutical composition comprising Spirulina polysaccharide was prepared as follows. Spirulina polysaccharide, lactose, corn starch and hydroxypropylcellulose were mixed at a ratio of Spirulina polysaccharide 260 mg, lactose 600 mg, corn starch 130 mg and hydroxypropylcellulose 10 mg, and the mixture was kneaded and granulated with a granulator having dies of 1 mm diameter, and the granules were dried at 60° C. for 50 minutes.

EXAMPLE 5

Formulation of food additive

The Spirulina polysaccharide powder was added to chocolate drink, tea, drinks, tablets, spice powder and hamburger at a concentration of 3%.

EXAMPLE 6

Formulation of feeds

The Spirulina polysaccharide was mixed with corn powder, brans, crude fish meal, plant meal after oil production, etc. to prepare feeds containing 5% Spirulina polysaccharide.

The Spirulina polysaccharide of the present invention has antiviral activity on human immunodeficiency virus (HIV) and other various pathogenic viruses, and therefore useful for an ingredient of antiviral pharmaceutical compositions, foods and drinks, especially functional foods and drinks, food additives, feeds, and the like.

We claim:

1. A method for prophylactic or therapeutic treatment of a viral disease, comprising administering to a subject to be treated an antiviral polysaccharide purified from an extract prepared by extracting Spirulina cells with hot water, wherein the antiviral polysaccharide is free of protein and has the following properties:

(1) it comprises rhamnose, glucose, fructose, ribose, galactose, xylose, mannose, glucuronic acid and galacturonic acid;

(2) it exhibits an absorption at 480 nm in phenol-sulfuric acid reaction; and (3) it has a molecular weight of 250,000 to 300,000 Daltons as determined by gel filtration.

2. A method according to claim 1, wherein the virus to be treated is selected from the group consisting of human immunodeficiency virus (HIV), herpes simplex virus, human cytomegalovirus, measles virus, mumps virus and influenza virus.

3. A method according to claim 1, wherein the virus to be treated is HIV.

4. A method according to claim 1 wherein the subject is human.

5. An antiviral polysaccharide purified from an extract prepared by extracting Spirulina cells with hot water, wherein the antiviral polysaccharide is free of protein and has the following properties:

(1) it comprises rhamnose, glucose, fructose, ribose, galactose, xylose, mannose, glucuronic acid and galacturonic acid;

(2) it exhibits an absorption at 480 nm in phenol-sulfuric acid reaction; and (3) it has a molecular weight of 250,000 to 300,000 Daltons as determined by gel filtration.

6. An antiviral polysaccharide according to claim 5 wherein the Spirulina is *Spirulina platensis*.

7. An antiviral polysaccharide according to claim 5, wherein the extraction is carried out at 70° C. to 95° C.

8. A pharmaceutical composition comprising the antiviral polysaccharide according to claim 5 and a pharmaceutically acceptable carrier or diluent.

9. A food or food additive to which the antiviral polysaccharide according to claim 5 has been added.

10. A feed or feed additive to which the polysaccharide according to claim 5 has been added.

* * * * *